United States Patent
Barberis et al.

(10) Patent No.: US 6,181,429 B1
(45) Date of Patent: Jan. 30, 2001

(54) INTERFEROMETER FOR MEASUREMENTS OF OPTICAL PROPERTIES IN BULK SAMPLES

(75) Inventors: Angelo Barberis, Milan; Stefano Caselli, Modena; Silvia Maria Pietralunga; Mario Martinelli, both of Milan, all of (IT)

(73) Assignee: Pirelli Cavi e Sistemi S.p.A., Milan (IT)

( * ) Notice: Under 35 U.S.C. 154(b), the term of this patent shall be extended for 0 days.

(21) Appl. No.: 09/218,297

(22) Filed: Dec. 22, 1998

Related U.S. Application Data
(60) Provisional application No. 60/068,864, filed on Dec. 29, 1997.

(30) Foreign Application Priority Data

Dec. 22, 1997 (EP) ................................. 97 122615

(51) Int. Cl.[7] ................................................ G01B 9/02
(52) U.S. Cl. ................................. 356/477; 356/484
(58) Field of Search ..................... 356/345, 349

(56) References Cited

U.S. PATENT DOCUMENTS

| | | |
|---|---|---|
| 5,268,739 | 12/1993 | Martinelli et al. . |
| 5,491,552 | 2/1996 | Knüttel . |

OTHER PUBLICATIONS

K. Minoshima et al., "Femtosecond time–released interferometry for the determination of complex nonlinear susceptibility", Optical Letters, vol. 16, No. 21, pp. 1683–1685, 1991.*

G.R. Olbright et al., "Interferometric measurement of the nonlinear index of refraction, $n_2$, of $CdS_x Se_{1-x}$ –doped glasses", Appl. Phys. Lett., vol. 48, No. 18, pp. 1184–1186, 1986.

K.I. Kang, et al., "Nonlinear–index–of–refraction measurement in a resonant region by the use of a fiber Mach–Zehnder interferometer", Applied Optics, vol. 35, No. 9, pp. 1485–1488, (1996).

L. Spager et al., "Time–resolved absolute interferometric measurement of third–order nonlinear–optical susceptibilities", Optical Society of America B, vol. 11, No. 6, pp. 995–999, (1994).

* cited by examiner

Primary Examiner—Robert Kim
(74) Attorney, Agent, or Firm—Finnegan, Henderson, Farabow, Garrett & Dunner, L.L.P.

(57) ABSTRACT

There is provided a method and apparatus for measuring the optical properties of bulk samples. A probe laser beam is fed into the two arms of the apparatus, a reference arm and a measurement arm, both of which contain optical fiber to conduct the laser lights. The measurement arm includes a free space area for mounting a sample to be tested. The probe beam is directed into the sample in free space. The sample also receives light in free space, rather than via the optical fiber, from a second, pump laser. The interaction of the sample and the pump laser affect the optical properties of the sample. This change in optical properties can be detected by comparing the output signals from the measurement and reference arms.

22 Claims, 4 Drawing Sheets

INTERFEROMETER FOR MEASUREMENTS OF OPTICAL PROPERTIES IN BULK SAMPLES

This application is based on European Patent Application No. 97122615.4 filed on Dec. 22, 1997 and U.S. Provisional Application No. 60/068,864 filed on Dec. 29, 1997, the content of which is incorporated hereinto by reference.

FIELD OF THE INVENTION

This invention relates to interferometers, and is directed toward an interferometer which is useful for measuring optically induced changes of the optical properties in samples of materials under study, e.g., temporally resolved optical nonlinearities. More specifically, the invention is directed to a hybrid interferometer which uses optical guides in the reference path and a combination of optical guides and free space propagation in the measurement arm.

BACKGROUND OF THE INVENTION

The role of nonlinear materials in high-speed applications such as optical switching, amplification, limiting and frequency conversion has created a need for an efficient method of characterizing nonlinear parameters. Many of these parameters can be characterized by the analysis of the index of refraction of a material. In particular, semiconductor materials exhibit a broad range of nonlinear effects with response times that span several orders of magnitude, owing to electronic nonlinearities, free-carrier effects, and thermal nonlinearities. Other materials may also exhibit properties which change over time, e.g., due to optical interaction or to environmental factors, and which also change the materials' index of refraction.

The presence of two or more nonlinear mechanisms can complicate the interpretation of optical nonlinearities because many techniques cannot distinguish between them. Quantitative information concerning the nonlinear index of refraction for optical materials is essential for the development of all-optical devices, such as opto-optical switches. Several techniques have been proposed for conducting this measurement, most of which are based on a direct interferometric measurement that uses a pump and probe technique.

One technique is to analyze temporal interference fringes to obtain the nonlinear index of refraction, as described in "Nonlinear-Index-Of-Refraction Measurement In A Resonant Region By The Use Of A Fiber Mach-Zehnder Interferometer", Applied Optics, Vol. 35, No. 9, Mar. 20, 1996, pages 1485–88. This technique uses fiber light guides in both the reference and measurement arms. Also included in each arm is an adjustable delay unit (AD) based on an optical fiber pigtailed graded index rod-lens pair, to vary the optical length of each arm.

The inventors have found that this technique is difficult to use to do measurements of bulk sample properties because of the difficulty in preparing an interface between the light guides in the measurement path and the sample to be measured. Often, it is possible that installing connecting light guides to the sample will result in some shift of its electrical properties. In addition, some samples cannot be connected directly to optical light guides.

Furthermore, according to this technique the pump pulses propagate in the optical fibers comprised in the interferometer arms; the inventors have observed that this sets a limit to the maximum pump power available for the measurements.

Another technique is disclosed in "Time-Resolved Absolute Interferometric Measurement Of Third-Order Nonlinear-Optical Susceptibilities", Journal of the Optical Society of America B, Vol. 11, No. 6, June 1994, pages 995–999. This technique, as illustrated in FIG. 1 of the paper, uses free space propagation of optical signals to measure nonlinear optical properties of bulk materials. A Mach-Zehnder interferometer compares the two beams (probe and reference) in amplitude and phase. The sample is located in the probe arm and interacts with the stronger collinear pump beam. The time delay $\tau$ between the pump and probe pulses provides the basis for a sampling interferometry.

The inventors have observed that the above techniques has disadvantages linked with using an optical measurement system wherein the light propagates completely in free space; in particular it is bulky and it needs careful alignment of all the optical components, what renders this technique difficult to use.

Other discussions of measurement of nonlinear properties can be found in "Femtosecond Time-Resolved Interferometry For The Determination Of Complex Nonlinear Susceptibility", Optics Letters, Vol. 16, No. 21, Nov. 1, 1991, pages 1683–1685 and "Interferometric Measurement Of The Nonlinear Index Of Refraction $n_2$ Of $CdS_xSe_{1-x}$-Doped Glasses", Applied Physics Letters, Vol. 48, No. 18, May 5, 1986, pages 1184–1186.

U.S. Pat. No. 5,268,739 discloses a laser apparatus for measuring the velocity of a fluid. In the system disclosed, a laser beam is fed into a pipe through which a fluid is flowing. Particles in the fluid interfere with the light. The velocity of the fluid is calculated from this interference.

SUMMARY OF THE INVENTION

Applicant has found that the optical properties of a sample can be measured without the need to attach light guides to the sample, while taking advantage of the beneficial properties of using light guides in a measurement apparatus, by using a hybrid interferometer which has a combination light guide and free space light path in its measurement arm. This arrangement greatly simplifies the testing of nonlinear optical properties of the samples under consideration.

More specifically, the inventors have developed a hybrid interferometer with a reference arm comprised of light guide paths and a measurement arm comprised of a combination of light guide paths and a free space area where the sample under test is located, and where coupling of a pump beam to the sample is conducted in free space.

According to a first aspect the present invention is related with an interferometer comprising:
  a first optical source for use as a source of a probe beam;
  a reference arm comprised of one or more optical guides for guiding a light signal from the first optical source to an output detector,
  a measurement arm comprised of a plurality of optical guides, a lens system, and a free space area for mounting a sample under test, so that the probe beam is guided through the sample;
  a second optical source for use as a source of a pump beam to be provided to the sample in the free space area; and
  a photodetector for detecting the changes in the optical properties of the sample by means of comparing the signal received from the reference arm with the signal received from the measurement arm.

In a preferred embodiment the optical guides are single mode optical fibers. A polarization controller is preferably included along one of said measurement or reference arm. Alternatively, the optical guides can be polarization maintaining optical fibers.

The interferometer preferably includes a coupler for combining the signal received from the reference arm and the signal received from the measurement arm into an interference signal and for coupling said interference signal to the photodetector.

According to preferred embodiments, the probe and pump beam are collinear within the sample, and the interferometer includes a selective reflector in the free space area for reflecting the pump beam to the sample and for transmitting the probe beam.

Possible embodiments for the selective reflector are a dichroic mirror or a polarizer.

A selective transmission device is preferably included in the free space area, for transmitting the probe beam and for preventing the pump beam from entering the optical guides. Possible embodiments for the selective transmission device are a dichroic mirror or a polarizer.

The interferometer can have a feedback circuit which includes a piezo controller for maintaining the interferometer in its quadrature condition. Also, the interferometer can have means for periodically modulating the phase of the signal along one of said reference or measurement arms.

According to a second aspect the present invention is related with a method of measuring the optical properties of a sample, comprising:

generating a probe laser beam;
propagating a portion of the probe beam in a first optical fiber and another portion of the probe beam in a second optical fiber;
mounting the sample in a free space area along said second fiber;
illuminating the sample in free space with a pump beam; and
comparing the outputs of the first and second fiber to determine the optical properties of the sample.

The optical properties detected can be the index of refraction and/or the absorption of the sample.

The step of comparing can comprise combining the output of the first and second fiber into an interference signal and measuring the interference signal intensity. The method can comprise the step of controlling by a feedback circuit the length of one of the first and second fiber so as to maintain a quadrature condition for the interference signal.

The method can comprise the step of periodically modulating the phase of a signal along one of the first and second fiber.

According to a third aspect the present invention is related with a method of measuring changes in an environmental condition which affects the optical properties of a sample, comprising:

generating a probe laser beam;
propagating a portion of the probe beam in a first optical fiber and another portion of the probe beam in a second optical fiber;
mounting the sample in a free space area along said second fiber;
illuminating the sample in free space with a pump beam;
comparing the outputs of the first and second fiber to determine the optical properties of the sample; and
determining the change in the environmental condition based change in the optical properties of the sample.

DESCRIPTION OF THE PREFERRED EMBODIMENTS

Figure 1:
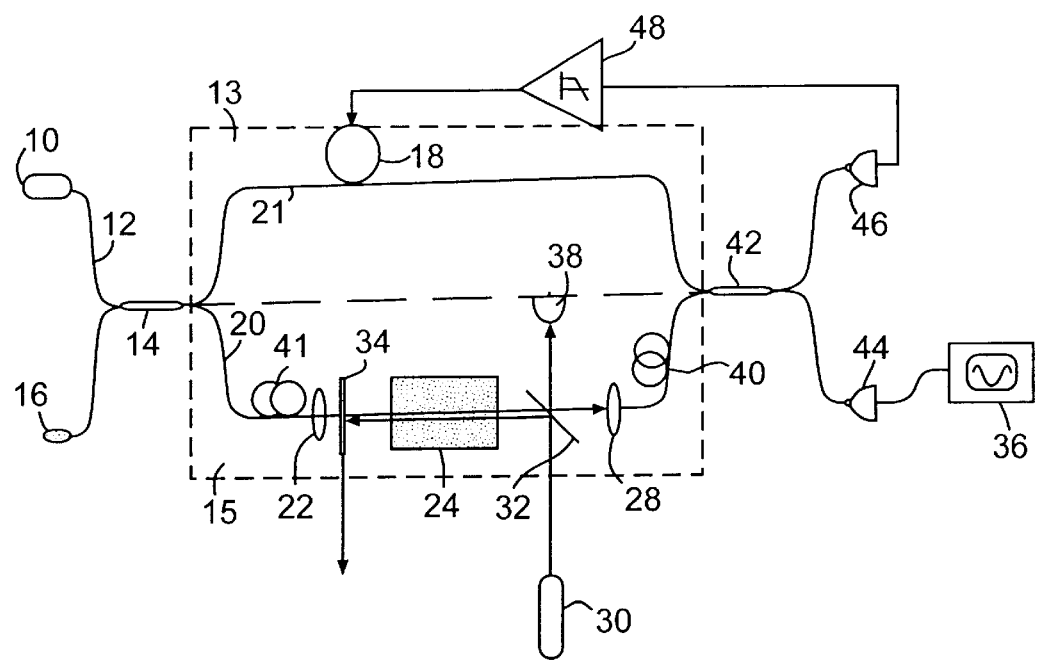
FIG. 1 illustrates a hybrid interferometer constructed in the Mach-Zehnder configuration.

Referring now to FIG. 1, there is provided a hybrid interferometer used to measure the optical properties of a sample under test. Two inputs are used to conduct the measurements. The first is a probe beam, which, in one embodiment, may have a wavelength of about 1.55 $\mu$m. This beam is generated by a semiconductor laser diode 10, with a narrow band (New Focus model 6262). The second input, a pump beam, is described herein. The probe beam is coupled into a step-index monomode optical fiber 12 (FOS model SM-R). A 50/50 fiber coupler 14 (Gould model 236246) splits the probe beam from the laser source between the reference arm 13 and the measure arm 15; the remaining input of the coupler 14 is terminated on an index-matching termination 16, to minimize back reflections.

Optical fiber of any known type other than the step-index type can be used for the interferometer. It is preferred, however, that the fiber be single-mode at the probe beam wavelength, to minimize phase noise at the interferometer output due to the different propagation times of different modes in multimode fibers.

The fiber 21 of the reference arm is coiled around a piezo ceramic disk 18 (Vernitron, $\Phi$=2 cm, 0.5 cm thick, $V_\pi$=100 V) that is inserted in a feedback loop to maintain the condition of quadrature for the interferometer (its point of maximum sensitivity). The feedback loop includes a photodetector 46 and piezo driver (or piezo controller) 48.

In the measurement arm the optical fiber 20 is interrupted at the sample location. The probe beam is collimated out of the fiber 20 by lens 22, enters the sample under test 24, and, after exiting it, is focused into the fiber 26 by lens 28.

An optical-fiber polarization controller 41 of a known type, comprising coils of monomode optical fiber, is preferably inserted along fiber 20 in the measurement arm 15 before lens 22 to control the polarization of the probe beam in the sample.

A pump optical beam, which induces the nonlinear phenomena in the sample, comes from a Q-switched Nd:YAG laser 30, emitting 10 ns pulses at 1060 nm (New Wave Research Inc.) and propagates in the sample under test collinear, superposed and counterpropagating with respect to the probe beam. Probe and pump optical beams are spatially gaussian, with 1/$e^2$ radius of respectively 100 $\mu$m and 400 $\mu$m.

The sample under test can be any material which is transparent to the probe beam wavelength. In particular it can be a solid, or a liquid or gas, e.g., enclosed in a cell with walls having low attenuation at the pump and probe wavelengths.

The measurement arm of the interferometer contains two dichroic mirrors 32 and 34, transmitting 1550 nm and reflecting 1060 nm (EKSMA). Mirror 34 prevents the pump beam from entering the optical fiber and reaching the probe beam source and the photodetectors; mirror 32 allows the beam from laser 10 and laser 30 to overlap in the sample under test and also acts to extract a portion of the beam from laser 30 as a trigger signal for the oscilloscope 36 at the output 38.

The measurement arm also contains two lenses 22 and 28. Lens 22 is a 0.25-PITCH gradient-index lens (SELFOC) and collimates the optical beam at the output of the fiber 20 through mirror 34 and into the test sample 24. Lens 28 is a biconvex BK7 lens of focal length f=8 mm and focuses the probe beam after it exits the sample 24 into the fiber 26. A second 50/50 fiber coupler 42 (E-TEK) creates the interference between the portion of the probe beam phase modulated by the pump beam and the portion of the probe beam that has traveled through the reference arm. An optical fiber polarization controller 40 of a known type, comprising coils of monomode optical fiber, is inserted into the measurement arm between lens 28 and fiber coupler 38 to match the polarization of the reference and measurement beams, and thus to maximize the visibility of the fringes of interference.

The two outputs of coupler 42 go to two photodetectors 44 and 46, which read the intensity modulated signals. This translates the phase difference between the reference and the measurement optical path. The signal from photodiode 44 (New Focus model 1611—1 GHz bandwidth) is monitored by an oscilloscope 36 for the time-resolved measurement of the dephasing signal. Any photodetector can be used instead of photodiode 44, provided that it responds to the probe beam wavelength and it has a bandwidth corresponding to the pump beam pulse duration and to the time scale of the optical phenomena to be detected in the sample under test. Oscilloscope 36 can be replaced by a streak camera if the signals to be detected have a very fast time scale, e.g., in the picosecond or sub-picosecond range. Photodiode 46 (New Focus model 1811—125 MHz bandwidth) provides the input signal for the feedback loop that controls piezo driver 48 to keep the interferometer operating at its quadrature point. Any photodetector can be used instead of photodiode 46, provided it has a bandwidth at least an order of magnitude greater than the bandwidth of the interferometer noise (vibrations, thermal drift, environmental noise, etc.) to be tracked. In the embodiment shown, the piezo controller comprises a simple electronic circuit, formed by a single-pole active integrator. Its pole frequency is 20 kHz, its open loop gain at zero frequency is equal to 250. The piezo controller further comprises a high voltage amplifier, for example, a Burleigh model PZ-70, with its pole frequency set at 5 kHz and its variable gain set at 50.

Figure 6:
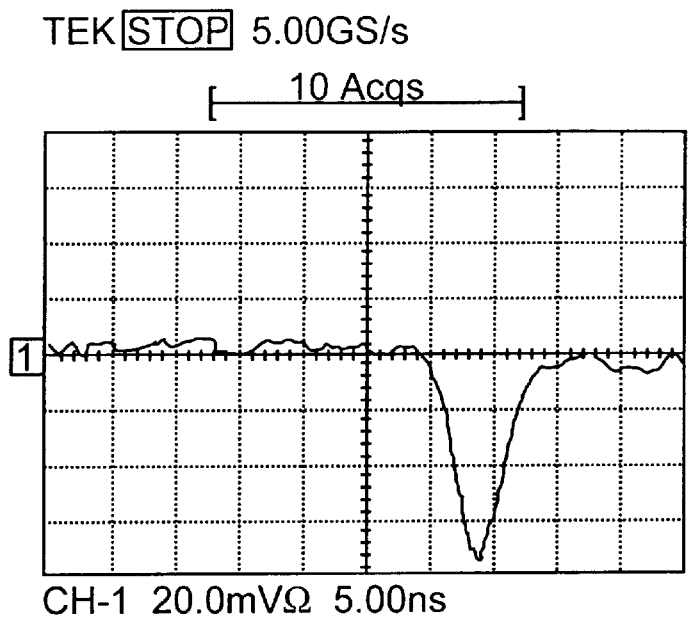
FIG. 6 illustrates the results of a measurement made with the interferometer of FIG. 1 on a sample of ZnS.

An example of an XPM (cross phase modulation) measurement done with the device of FIG. 1 is given in FIG. 6, showing an oscilloscope plot of the interferometer output intensity (arbitrary units) against time (5 ns/division) for a ZnS sample, with probe and pump beam having different wavelengths as above described. A non-resonant nonlinearity was observed and a coefficient $n_2=3.56 \cdot 10^{-19}$ m$^2$/W for the sample was calculated from the measurement results.

Figure 7:
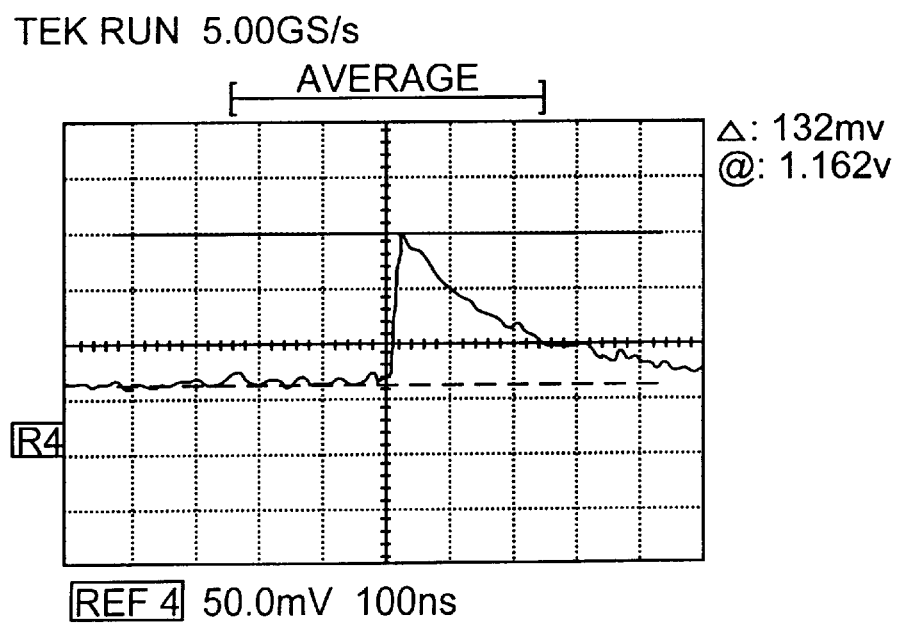
FIG. 7 illustrates the results of a measurement made with the interferometer of FIG. 1 on a sample of CdTe:ln.

FIG. 7 shows another test result, relating to a measurement made on a CdTe:In sample. An oscilloscope plot of the interferometer output intensity (arbitrary units) against time (100 ns/division) with the same test device and conditions as above described shows a resonant nonlinearity in the sample under test. Based on the test measurement, lifetime of photogenerated carriers was determined to be $\tau=180$ ns, while the refractive index change per photogenerated carrier was determined to be $\sigma_r=-1.2 \cdot 10^{-27}$ m$^3$.

The disclosed embodiment has counterpropagating pump and probe beam. It is also possible to have the pump and probe beams copropagate, by exchanging the position of mirrors 34 and 32. A copropagating pump and probe configuration can also be implemented with the embodiments that will be described in the following. However, a counterpropagating configuration is preferred, in order to minimize coupling of residual pump leaking through the dichroic mirror to photodetector 44, and to prevent saturation of the same.

Another possibility is that the probe and the pump are non-collinear. For example, the sample under test can be side-pumped or, in general, the pump and probe beams can form a non-zero angle within the sample. The pump power needed to achieve a given change in the optical properties of the sample can be in this case significantly greater than in a collinear arrangement.

Other variations on this architecture may be realized without departing from the scope and purposes of the invention. For example, any optical wavelength which is compatible with transmission in optical fibers can be chosen for the probe beam. The sample under test must sufficiently transmit the optical wavelength. Preferably, to minimize phase noise, the probe beam wavelength is such as to allow monomode propagation in the optical fibers, optical fiber couplers and other optical fiber components (such as polarization controllers) comprised in the interferometer, as explained above.

The choice of probe beam source 10 in terms of linewidth and coherence length depends on the effective unbalancing of the interferometer, i.e., the difference in optical length between the reference and measurement arm. The condition for correct operation is that unbalancing be less than or equal to the coherence length of the laser source. Once this condition is satisfied, no restriction is made on the laser to be chosen for the probe source 10. Probe source 10 can provide a CW output or, alternatively, can have a modulated, pulsed or chopped output.

Pump source 30 may be chosen to be any source, free-space emitting at any wavelength of interest, having a continuous or variable output power. The pump beam interacts with the sample under test and only with a limited part of the interferometer structure, namely mirrors 32 and 34 in the measurement arm, while the remaining parts of the interferometer, including all the waveguided paths, are subject only to the relatively low power probe beam. Accordingly, the interferometer can be used even with pump sources providing very short pulses of relatively high peak power. In particular Q-switched or mode-locked laser sources emitting pulses in the nanosecond, picoseconds or sub-picosecond range, or time-compressed laser pulse sources, can be used as pump sources to measure the transient nonlinear behavior of the sample under test in a corresponding time scale.

Either of probe source 10 and pump source 30, or both, can emit polarized radiation or be followed by a polarizer, in order to allow measurement of polarization dependent optical phenomena.

In another embodiment the interferometer can be heterodyned. Heterodyning allows independent and simultaneous measurement of optically induced variations in both refractive index and optical absorption (respectively, the real and the imaginary components of the complex refractive index) of the sample under test. This is specially useful for measuring resonant optically induced nonlinear phenomena, that are associated with changes in optical absorption. Heterodyning is achieved by superposing a periodic phase modulation along one of the interferometer arms and by demodulating the signal at the output of photodetector 46 according to known techniques. A phase modulation can be achieved by feeding a periodic signal to the piezoceramic disk 18 or by connecting a phase modulator along one of the interferometer arms, normally along the reference arm. The phase modulation is preferably of a saw tooth shape, to achieve a corresponding sinusoidal modulation at the interferometer output.

Slight modifications can be made to the measurement arm of the interferometer, in order to use it with spectrally variable pump beam. One possibility is to provide pump and probe beams respectively with vertical and horizontal polarization and to use polarization—instead of wavelength—for beam coupling, by replacing the dichroic mirrors M1 and M2 by two linear sheet polarizers or, e.g., by two polarizing beamsplitters. In this case the pump beam is preferably polarized. In this embodiment the pump beam wavelength can be selected to be substantially equal to the probe wavelength (degenerate case) as well as to be different from the probe wavelength (non-degenerate case).

Figure 2:
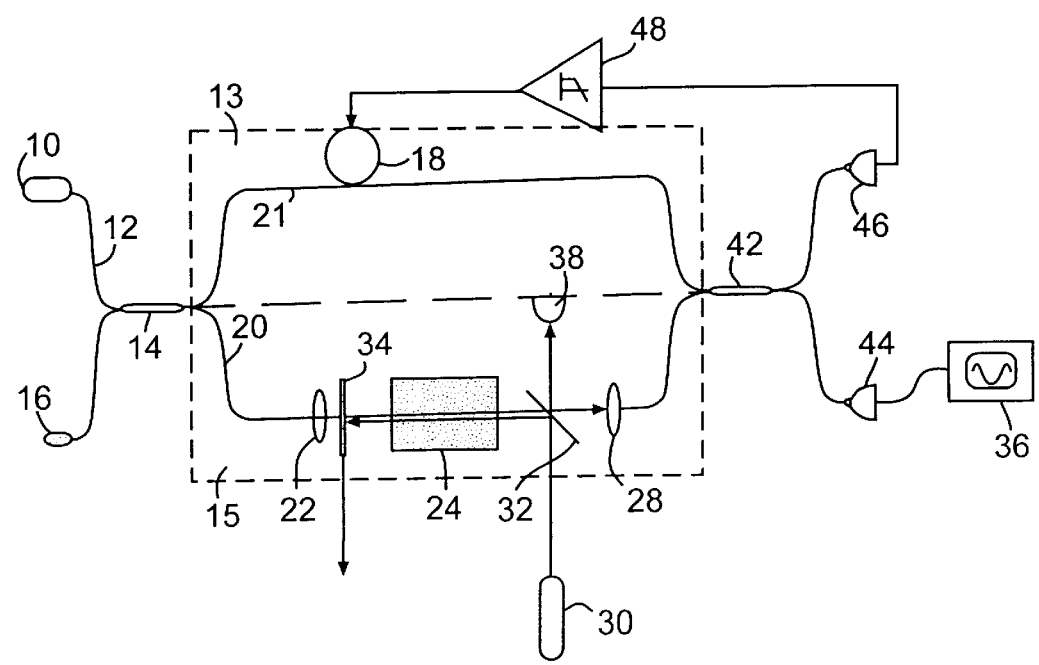
FIG. 2 illustrates another embodiment of the above interferometer.

It is possible to eliminate the need for polarization controllers in the device according to the previous embodiment if, as shown in FIG. 2, polarization maintaining fiber couplers are used for couplers 14 and 42 and both the reference and measurement arm are made of polarization maintaining (high-birefringence) monomode optical fiber, for example of the PANDA™-type.

Figure 3:
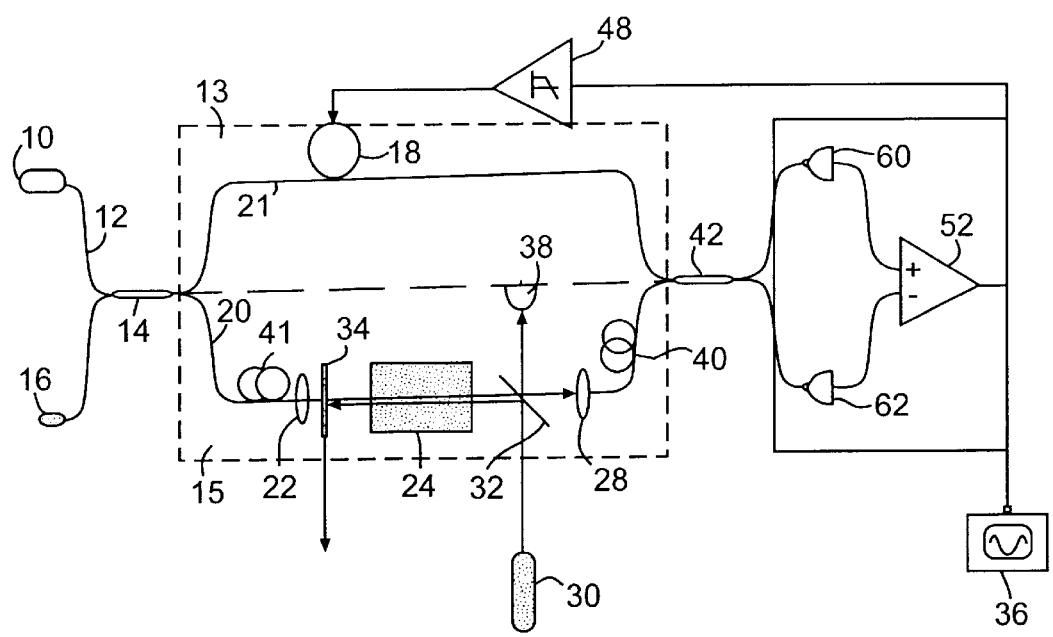
FIG. 3 illustrates another embodiment of the above interferometer.

As shown in FIG. 3, another embodiment of the present invention includes the addition of a differential detection apparatus, comprising photodiodes 60 and 62 and differential amplifier 52. Preferably photodiode 60 and 62 both have a bandwidth corresponding to the pump beam pulse duration and to the time scale of the optical phenomena to be detected in the sample under test. Differential amplifier 52 preferably is a transimpedence amplifier and performs differential amplification of the optically generated currents from photodiodes 60 and 62. Photodiodes 60 and 62 and amplifier 52 can either constitute independent and connecting blocks (for example, photodiodes followed by transimpedence preamplifiers, followed by a differential voltage amplifier) or the functionality can be accomplished by a single stage comprising two photodiodes and a transimpedence differential amplifier. The differential output signal from differential amplifier 52 drives both the feedback loop piezo controller 48 and the oscilloscope 36, which is used to record the temporal behavior of the interference signal.

Figure 4:
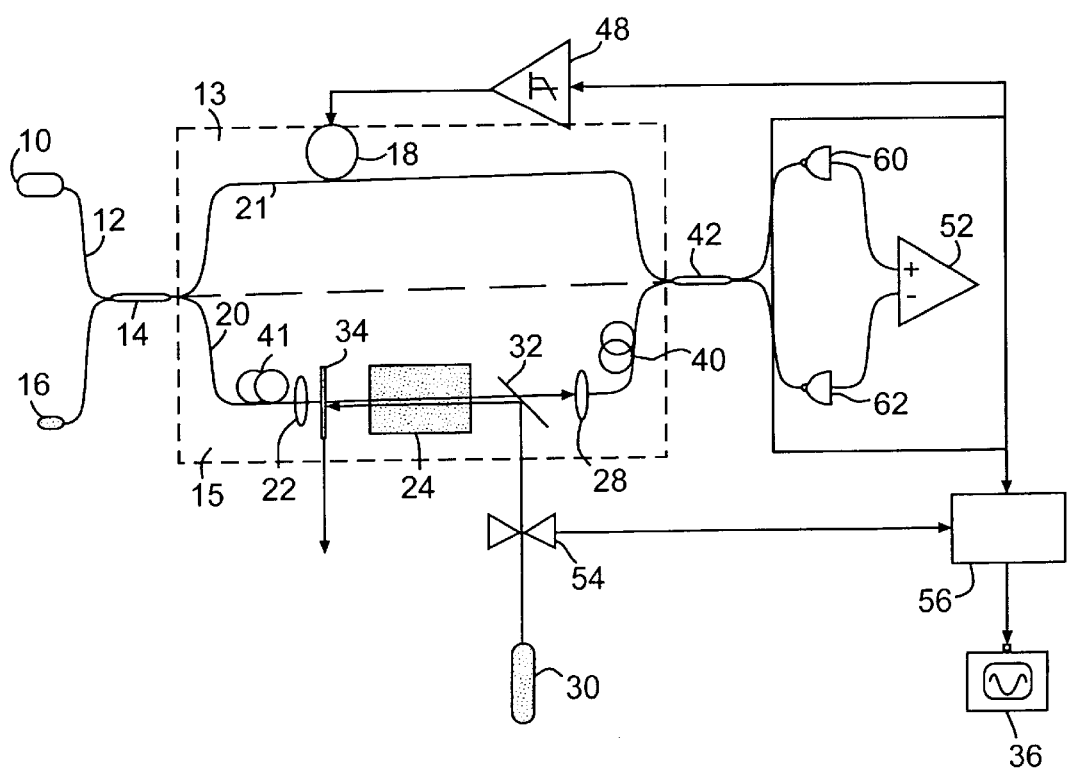
FIG. 4 illustrates another embodiment of the above interferometer.

FIG. 4 shows yet another embodiment of the present invention. FIG. 4 includes all the elements of FIG. 3 with the addition of an optical chopper 54, which can also be replaced by an optical modulator for the pump beam. This optical chopper 54 is connected to a lock-in detection system 56, which is used to supply signals to a fast digital oscilloscope 36.

Figure 5:
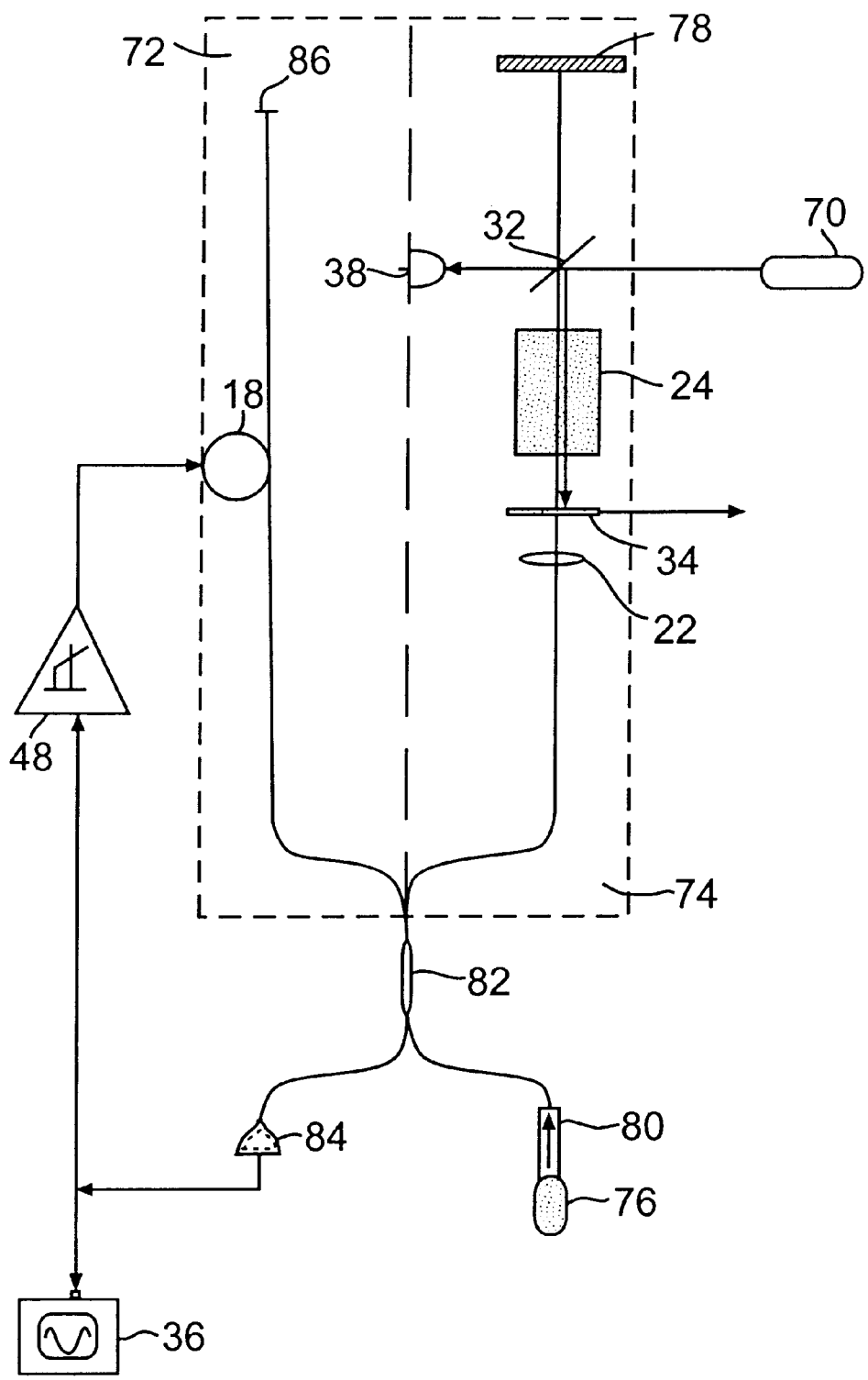
FIG. 5 illustrates a hybrid interferometer constructed in the Michelson configuration.

Finally, FIG. 5 illustrates how the hybrid light guide/free space measurement concept can be applied using a Michelson architecture type device. In FIG. 5 laser source 76 is used as the probe beam. This may be a continuous wave laser emitting at a wavelength of around 1.5 $\mu$m; however, any wavelength can be adopted, as long as it is compatible with the optical fiber used for monomode propagation. A linear state of polarization is required for the light of the probe beam, oriented as one of the eigen axes of the high-birefringent optical fibers that make up the reference arm 72 and the measurement arm 74 of the device. An optical isolator 80 is provided between the output of probe beam source 76 and an end of a 3 dB monomodal polarization maintaining fiber coupler 82, having two other ends connected to the reference arm 72 and to the measurement arm 74 of the interferometer. Reference arm 72 has an optical fiber ended by a mirror 86. Mirror 86 can be made, for example, by mirroring the fiber end according to known techniques. A fourth end of coupler 82 is connected to a photodetector 84 suitable for reading an interferometer dephasing. The photodetector output is directed to a piezo controller 48 driving a piezo ceramic disk 18. As previously described with reference to the previous embodiments, heterodyning of the interferometer may be provided by known means.

A free-space section is provided in the measurement arm 74, comprising a collimating lens 22, planar sheet polarizers 34 and 32 and a mirror 78. Polarizers 34 and 32 can be replaced by polarizing beam splitters. A sample under test can be positioned in the free space region between polarizers 34 and 32. Also provided is laser 70, a laser source for the pump beam. This typically operates in a pulse mode. In an example laser 70 is Q-switched with pulses at 10 nanoseconds FWHM, emitting at a wavelength of 1.064 $\mu$m. This pump beam, however, can operate at any wavelength which is interesting for the phenomena to be measured, and may be either modulated or mode locked or Q-switched. It is believed that the remaining details and operation of this configuration would be obvious to those of ordinary skill in the art based on the previous description of the other embodiments, and will not be repeated here.

Applicants observe that a Mach-Zehnder architecture for a hybrid light guide/free space interferometer has advantages over a Michelson architecture, at least in that it is less prone to noise and in that it provides a better protection of a measuring photodetector against coupling of pump beam radiation thereto due to unwanted reflections or to non-ideal behavior of dichroic mirrors or polarizers.

Those skilled in the art would also appreciate that the lenses used to focus the light beam from the light guides into the sample under test, and from the sample under test into the light beams, can be replaced by any optical system which is effective to respectively collimate the optical beam. In addition, for both the Mach-Zehnder and the Michelson configurations, either birefringent fibers or low birefringence single-mode fibers may be used. Either direct or differential detection can be used, and either dichroic mirrors or polarizers may be used in the structure.

Although the above description is focused mainly on the construction of the interferometer itself, the invention may be used as part of an apparatus for measuring any change in the physical surroundings of the object under test. For example, if the test sample has an index of refraction which changes with slight changes in temperature, the above device may be used as an accurate detector of temperature change. Similarly, other environmental conditions which may cause a change in the index of refraction of test materials may be monitored using the above-described invention.

As is obvious from the above, there are several design choices which will be made to vary the structure of the interferometer without departing from the scope and spirit of the invention, as described above and claimed herein.

What is claimed is:

1. An interferometer comprising:
   a first optical source for use as a source of a probe beam;
   a reference arm comprised of one or more optical guides for guiding a light signal from the first optical source to an output detector, a measurement arm comprised of a plurality of optical guides, a lens system, and a free space area for mounting a sample under test, so that the probe beam is guided through the sample;

a second optical source for use as a source of a pump beam to be provided to the sample in the free space area; and a photodetector for detecting the changes in the optical properties of the sample by means of comparing the signal received from the reference arm with the signal received from the measurement arm.

2. An interferometer as in claim 1, wherein the optical guides are single mode optical fibers.

3. An interferometer as in claim 2, also including a polarization controller along one of said measurement or reference arm.

4. An interferometer as in claim 1, where the optical guides are polarization maintaining optical fibers.

5. An interferometer as in claim 1, also including a fiber coupler for combining the signal received from the reference arm and the signal received from the measurement arm into an interference signal and for coupling said interference signal to the photodetector.

6. An interferometer as in claim 5, wherein the probe and pump beam are collinear within the sample.

7. An interferometer as in claim 6, also including a selective reflector in the free space area for reflecting the pump beam to the sample and for transmitting the probe beam.

8. An interferometer as in claim 7, wherein the selective reflector is a dichroic mirror.

9. An interferometer as in claim 7, wherein the selective reflector is a polarizer.

10. An interferometer as in claim 7, also including a selective transmission device in the free space area for transmitting the probe beam and for preventing the pump beam from entering the optical guides.

11. An interferometer as in claim 10, wherein the selective transmission device is a dichroic mirror.

12. An interferometer as in claim 10, wherein the selective transmission device is a polarizer.

13. An interferometer as in claim 5, also including a feedback circuit which includes a piezo controller for maintaining the interferometer in its quadrature condition.

14. An interferometer as in claim 5, also including means for periodic phase modulation of the signal along one of said reference or measurement arms.

15. A method of measuring optical properties of a sample, comprising:

generating a probe laser beam;

propagating a portion of the probe beam in a first optical fiber and another portion of the probe beam in a second optical fiber;

mounting the sample in a free space area along said second fiber;

illuminating the sample in free space with a pump beam; and comparing the outputs of the first and second fiber to determine the optical properties of the sample.

16. A method of measuring the optical properties of a sample as in claim 16, wherein index of refraction is the optical property detected.

17. A method of measuring the optical properties of a sample as in claim 16, wherein absorption is the optical property detected.

18. A method of measuring the optical properties of a sample as in claim 15, wherein the step of comparing comprises using a fiber coupler to combine the output of the first and second fiber into an interference signal and measuring the interference signal intensity.

19. A method of measuring the optical properties of a sample as in claim 18, comprising the step of controlling by a feedback circuit the length of one of the first and second fiber so as to maintain a quadrature condition for the interference signal.

20. A method of measuring the optical properties of a sample as in claim 18, comprising the step of periodic phase modulation of a signal along one of the first and second fiber.

21. A method of measuring changes in an environmental condition which affects the optical properties of a sample, comprising:

generating a probe laser beam;

propagating a portion of the probe beam in a first optical fiber and another portion of the probe beam in a second optical fiber;

mounting the sample in a free space area along said second fiber;

illuminating the sample in free space with a pump beam;

comparing the outputs of the first and second fiber to determine the optical properties of the sample; and determining the change in the environmental condition based on the change in the optical properties of the sample.

22. A method of measuring the optical properties of a sample as in claim 21, wherein the step of comparing comprises using a fiber coupler to combine the output of the first and second fiber into an interference signal and measuring the interference signal intensity.

* * * * *